SUGARCANE
Filed April 20, 1967 4 Sheets-Sheet 1
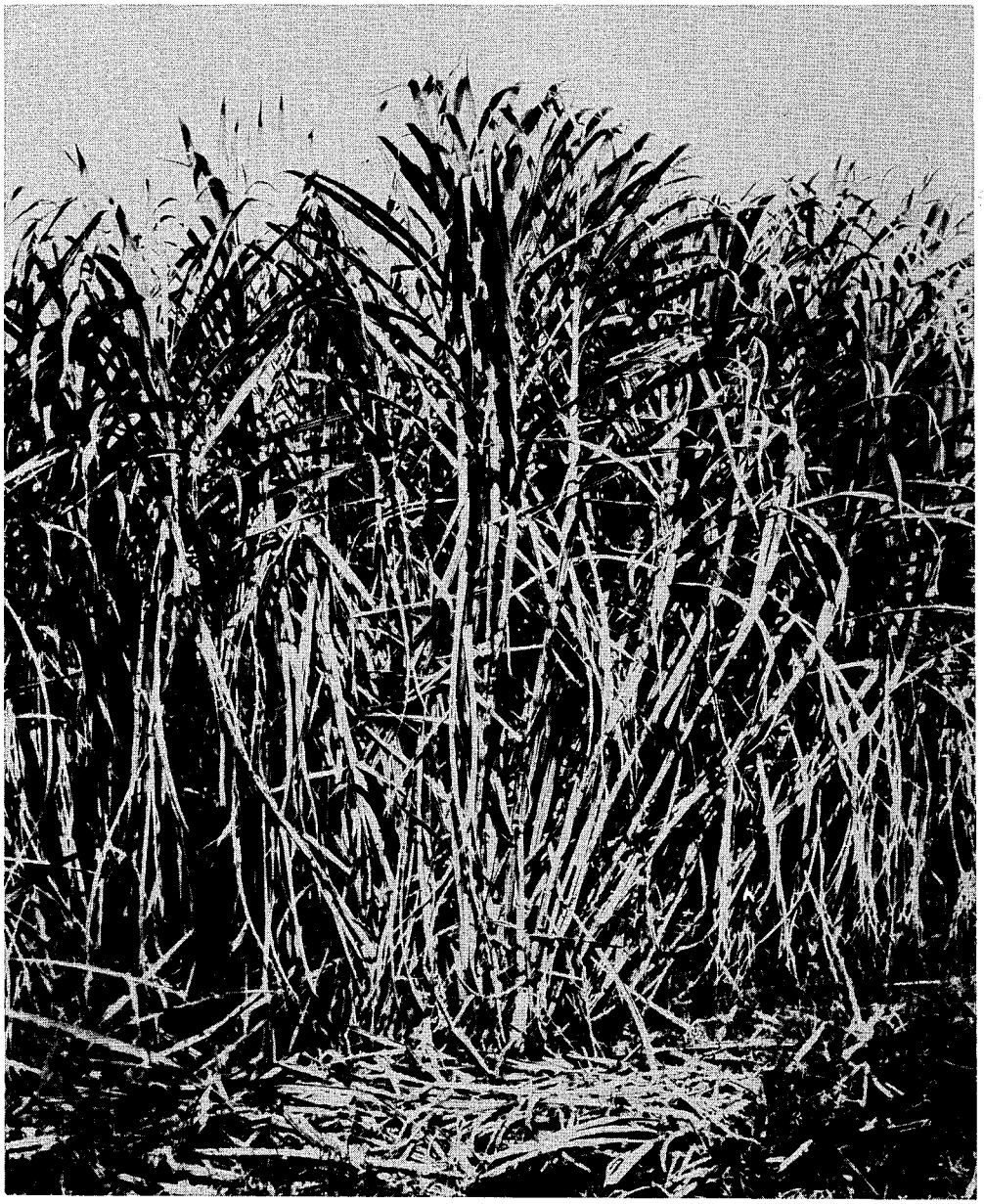
FIG. I
INVENTORS
LESLIE M. WEETMAN
BENJAMIN A. BOURNE
By
Cushman, Darby & Cushman
ATTORNEYS

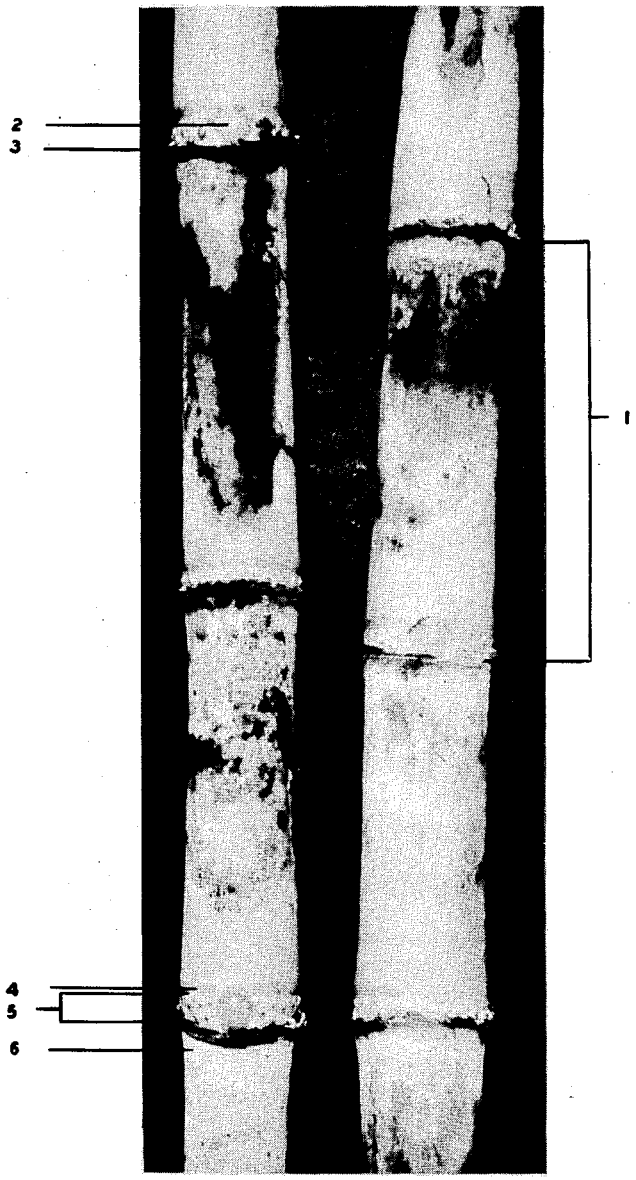
FIG. II
INVENTORS
LESLIE M. WEETMAN
BENJAMIN A. BOURNE
By
Cushman, Darby & Cushman SUGARCANE
Filed April 20, 1967 4 Sheets-Sheet 3
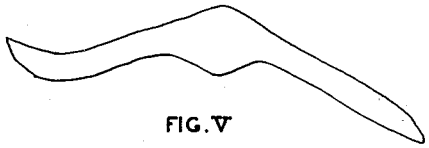
FIG. V
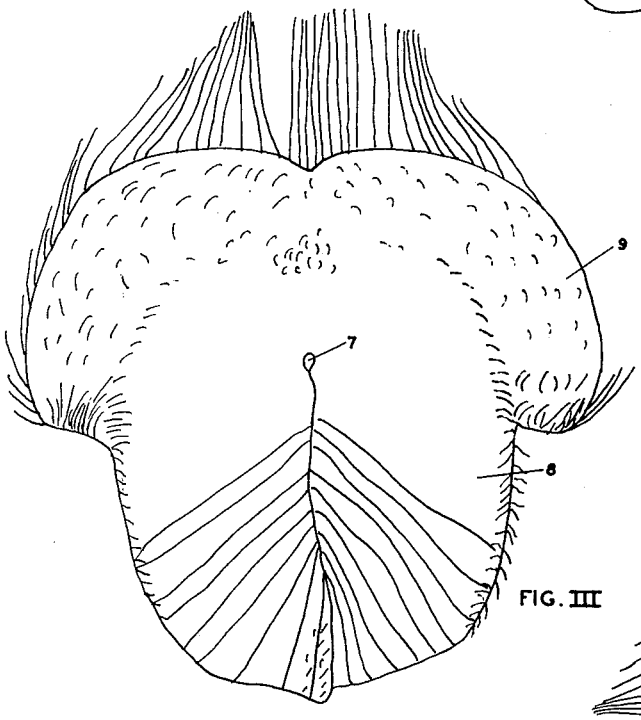
FIG. III
ANTERIOR
FIG. VII
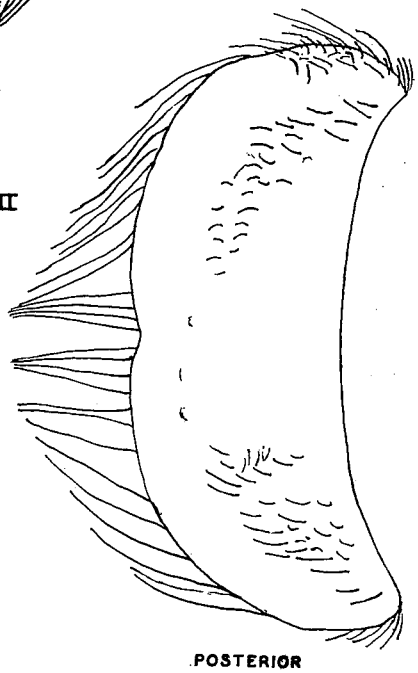
POSTERIOR
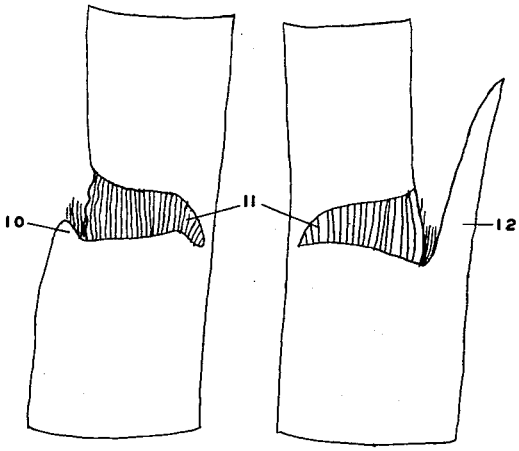
FIG. IV
INVENTORS
LESLIE M. WEETMAN
BENJAMIN A BOURNE
By Cushman, Darby & Cushman
ATTORNEYS

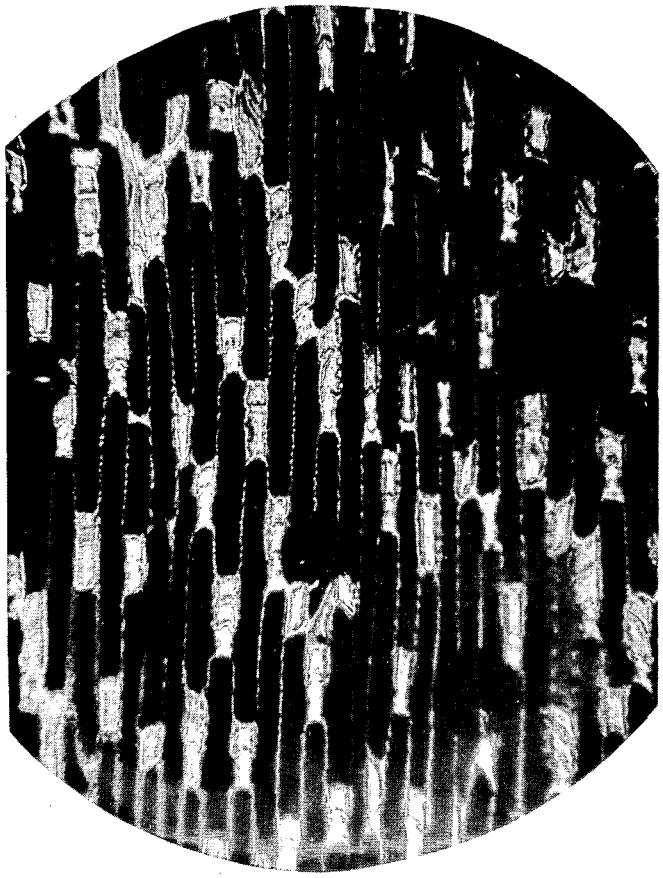
FIG. VI
INVENTORS
LESLIE M. WEETMAN
BENJAMIN A. BOURNE
By Cushman, Darby & Cushman
ATTORNEYS United States Patent Office Plant Pat. 2,846
Patented Nov. 12, 1968

2,846
SUGARCANE

Leslie M. Weetman and Benjamin A. Bourne, Clewiston, Fla., assignors to United States Sugar Corporation, Clewiston, Fla., a corporation of Delaware Filed Apr. 20, 1967, Ser. No. 632,458
1 Claim. (Cl. Plt.—89)

This new variety of sugarcane originated as a seedling produced by crossing the variety Cl. 47–143 as female and the variety Cl. 49–8 as male. (In this form of variety designation, which is well-known to sugarcane breeders, "Cl." denotes the breeding locality or station, i.e., Clewiston, Fla.; "49" represents the year that the particular variety was first grown, i.e., 1949; and "82" is the distinctive number assigned to that variety among those grown in that year.) The cross was made in November 1953, at Clewiston, Fla., and this new variety was selected from among the progeny of the cross. The inventors have subsequently propagated the variety at Clewiston, Fla., by means of stem cuttings under the identifying number Cl. 54–532.

In a trial replicated six times, extending over three crop years in an average moderately warm-land situation approximately three miles south of Lake Okeechobee, juice analyses were made in mid-November each year. The average indicated yield of 96° sugar per ton of cane for our new variety was 239.6 pounds as contrasted to only 198 pounds for the standard variety Cl. 41–223. Our new variety retains this high sucrose level until late in the season. Total sugar yield per acre for three crop years, based on the November analyses was 15.69 tons for our new variety and 13.01 tons for Cl. 41–223, the least significant difference being 1.38 tons.

Our new variety was also planted in a trial replicated five times on cold marginal land, consisting of typical low-mineral organic Everglades peat, in August 1962. In the following mid-December and toward mid-January, it was subjected to below-freezing temperatures on several successive days whereby all above-ground parts of the cane were killed. Subsequently the variety grew up again to a perfect stand and with good vigor and stooling, indicating that it is resistant to winter killing. Juice analyses were made on this replicated trial in early November for four successive crop years. Indicated yields of 96° sugar per ton of cane averaged 204.6 pounds for our new variety as compared to 148.6 pounds for the standard variety Cl. 41–223 and 153.8 pounds for C.P. 50–28. Total yields of sugar per acre for the four crop years were 17.83 tons for our new variety, 11.32 tons for Cl. 41–223, and 13.43 tons for C.P. 50–28, the least significant difference being 1.23 tons for the entire trial of 24 varieties.

Observations on the reaction of this new variety to our major cane diseases during the past decade have shown that it is susceptible to the brown stripe leaf disease caused by the fungus *Cochliobolus stenospilus* (Drech.) Mat. and Yam. However, it is quite resistant to the fungus diseases "pokkah boeng" caused by *Gibberella moniliformis* (Sheldon) Wineland, red rot caused by *Physalospora tucumanensis* Speg and the mosaic virus strains found in Florida, viz: A, B, D and E (a typical) by artificial inoculation. Under natural exposure to mosaic under field conditions, it has so far remained free from infection.

A long term study has been made over a period of three crop cycles to determine its reaction to the ratoon stunting virus and to the effect of the hot air seed treatment at 50° C. for 24 hrs. normally given to rid the plants of this disease. The experiments were conducted in randomized blocks and replicated five times in 1/60th acre plots on uniform, low mineral organic soil. While the heat treatment showed a slight decline in percent yield of 96° sugar in the cane, whether harvested early in mid-November or late February, this reduction in sucrose quality was never statistically significant and only amounted to an average in terms of percent yield 96° sugar points of 0.23 if cut early and between 0.06 and 0.19 point when cut late. The heat treated, ratoon stunting virus free cane, however, showed mean increases in tons of cane per acre for all three crop cycles, amounting to 0.56 ton the first year, 3.57 tons the 2nd year and 1.59 tons the third year. However, only the 2nd year results were significantly improved by an average of 0.13 ton per acre. An examination of the experimental data also showed that heat treatment to eliminate the ratoon stunting virus failed to show a significant improvement in the tons 96° sugar per acre, either for the first or third crop cycles, whereas the first stubbles averaged 0.47 ton improvement in this factor and a significant margin of 0.04 ton (80 lbs.) at the 5% level of significance, worth with sugar selling at 7.12¢ lb.—$5.70 per acre. In view of the advantages of heat treatment for eliminating ratoon stunting disease should plants become infected accidentally, this treatment is recommended for this variety when used commercially unless disease free seedcane is available, because no significant detrimental effects result from this treatment, as is sometimes the case with some cane varieties.

In the drawings:

FIGURE I is a photographic view showing the habit of growth of mature cane of this new variety;

FIGURE II is a photographic view of approximate mid-sections of typical stalks, showing internode 1, stem bud 2, leaf scar 3, growth ring 4, root band 5, and wax ring 6;

FIGURES III and VII show anterior and posterior views of the prophyll (or outermost bud scale) of the stem bud, showing germ pore 7, central disk 8, and wing 9;

FIGURE IV is a view of the two separated and flattened halves of the upper part of a leaf sheath, showing the outer auricle 10, the dewlap or blade joint 11, and the inner auricle 12;

FIGURE V is a view showing the outline of a ligule after its removal from the inner surface of the leaf sheath; and FIGURE VI is a photomicrographic view showing the pattern of the stem epidermal cells, magnified 450 times.

DETAILED DESCRIPTION

In the following detailed description of the new variety of sugarcane, the terminology employed in morphological description and numbering of hair groups is that employed by Artschwager (see Sugarcane (*Saccharum officinarum* L.): Origin, Classification, Characteristics, and Description of Representative Clones by Ernst Artschwager and E. W. Brandes. Agriculture Handbook No. 122. United States Department of Agriculture, 1958). Color descriptions are made by referring to the plates of Maerz and Paul (see A Dictionary of Color, second edition, by A. Maerz and M. Rea Paul. McGraw-Hill Book Company, 1950).

*The stalk (or culm)*

*Habit of growth* (see FIGURE I).—In years without strong winds the stalks are semi-erect in habit. The internodes are generally quite straight in alignment.

*Size.*—The stalks are generally 8 or 9 or more feet long in mature cane. They are nearly circular in cross-section, averaging 23.7 x 25.6 millimeters in the middle part of the stalk. The larger diameter may vary from 21 to 30 millimeters.

*Flesh.*—The color of the flesh often approximates Maerz' and Paul's designation 13–G–2, but is variable. The flesh is solid and of medium fiber content.

*Internodes* (1, FIGURE II).—They are cylindrical to slightly conoidal in shape and vary from about 9 to 15 centimeters in length in the middle parts of the stalks, averaging 12.75 centimeters. There are generally no bud furrows. There are occasional growth cracks.

*Color.*—The basic rind color just above the growth ring on young unexposed internodes is approximately Maerz' and Paul's 10–G–2, but many young internodes are also streaked with light green. The rind soon becomes covered with a moderate layer of wax which in turn becomes splotched with black from mold growth. The wax ring (6, FIGURE II) is well demarcated, although the wax is only moderately thick.

*Growth ring* (4, FIGURE II).—It is 1 to 3 millimeters in height, generally about 2. The color is greenish-white on young nodes, approximately Maerz' and Paul's designation 11–H–5 on mature ones.

*Root band* (5, FIGURE II).—It is 6 to 7 millimeters tall and slightly obconoidal in shape. The color is similar to that of the internode. There are two rows of root primordia. The primordia tend to germinate on older stalks and often there are roots an inch or more long high on the stalks.

*Leaf scar* (3, FIGURE II).—The leaf scar protrudes moderately under the bud. It may also be slightly depressed under the bud.

*Epidermal cells* (FIGURE VI).—The pattern formed by the cells of the stem epidermis is a combination of the types described by Artschwager and may be designated types 1+7+2. About one-half of the small cell groups consist of one cork cell associated with one silica cell (type 1). A somewhat smaller number (perhaps 35 to 40%) consist of two cork cells with one silica cell (type 7), and a still smaller number (10 to 15%) have no silica cells and consist only of a single (occasionally two) cork cell (type 2). A few of the cork cells are pointed although most have squarish ends. There are approximately 725 small cell groups per square millimeter. The average width of the long cells is about 9.5 microns. There are very few stomata in the epidermis, averaging about one per 2 square millimeters of surface.

*Stem buds*

*General characteristics.*—The buds (2, FIGURE II) are inserted at the leaf scar or slightly above. The tips extend to the growth ring. The buds are plump but are not protruding nor overly prominent. They average about 9.9 millimeters high by 10.5 millimeters wide. The central disk (8, FIGURE III) of the prophyll is oval in shape, and this is capped by the very broad wing which is about 50% broader than the central disk.

*Wings of the prophyll* (9, FIGURE III).—The wing is very broad and is attached at about the middle of the prophyll. The apex is broad and rather flat, with a notch between the two lateral halves.

*Pubescence.*—Pubescence is conspicuous mainly along the margins of the buds, particularly groups 15 and 4. Groups 1, 2, 13, 14, 16, 22, and 26 are also present.

*The leaf*

*The blade.*—The blades are spreading in habit. The larger leaves on each stalk are 4.3 to 5.4 centimeters in width, averaging 5.0, and are 127 to 168 centimeters in length, averaging 146. The ratio of the length to the width thereof averages 29.3.

*The sheath.*—The sheaths have an average length of approximately 12 centimeters in the middles of the stalks. They adhere moderately to the stalks, not falling off naturally, but they are easily pulled off. The dorsal field of pubescence (group 57) is about 13 to 15 centimeters long, beginning at a point about 5 centimeters below the dewlap, broadening to 2 centimeters wide in the middle then narrowing again to a point below. The hairs are moderately thick, appressed and spinelike. Group 60 hairs are few or none.

*Dewlaps* (11, FIGURE IV).—The color of the dewlap varies from about 13–L–2 to 14–K–1 in the plates of Maerz and Paul. The shape is largely deltoid to broad ligulate. Most of the outer surface is covered with group 58 hairs, being dense toward the outer margin and sparse toward the midrib. Group 52 hairs cover most of the inner surface, varying from sparse to dense. They sometimes extend across the midrib. Groups 55 and 65 are not evident. Group 51 consists of conspicuous long hairs (to 10 millimeters) near the outer margins.

*Auricles.*—The outer auricle (10, FIGURE IV) is usually short deltoid in shape and from 2 to 4 millimeters in height. The inner auricle (12, FIGURE IV) is long lanceolate and varies from 15 to 40 millimeters in height. The inner edge of the outer auricle and the base of the inner edge of the inner auricle have conspicuous hairs of group 54.

*Ligules* (FIGURE V).—The ligule is broadly and irregularly crescent-shaped with broad lozenge. It is about 8 millimeters tall in the middle and about 40 millimeters long. Both the upper and lower margins are irregularly dentate. Marginal cilia are about ¼ to ⅓ millimeter tall and grow mostly on the teeth of the upper margin thus accentuating the toothed appearance.

*Inflorescence*

In Clewiston, Fla., this new variety usually blooms abundantly in late November and early December. It is male sterile in this location.

Important characteristics which, in combination, help to distinguish this new variety of sugarcane from all other known varieties are:

(1) Early maturity.

(2) Relatively high yielding capacity on cold marginal land near Clewiston, Fla.

(3) Susceptibility to brown stripe disease.

(4) High resistance to pokkah boeng and red rot.

(5) Resistance to mosaic strains A, B, D, and E (atypical) by artificial inoculation.

(6) Moderately susceptible to the ratoon stunting disease virus.

(7) Stalks nearly circular in cross-section, averaging 23.7 x 25.6 millimeters in the middles of the stalks.

(8) Medium percent fiber in the stalks.

(9) Bud furrows generally absent.

(10) Growth ring 1 to 3 millimeters in height, generally about 2.

(11) There are two rows of root primordia.

(12) The stem epidermal pattern is type 1+7+2, the type 7 cells being nearly as numerous as the type 1 cells.

(13) There are approximately 725 small cell groups per square millimeter in the epidermis.

(14) There are very few stomata in the epidermis.

(15) Tips of the stem buds extend to the growth ring.

(16) The central disk of the prophyll is oval in shape and is capped by the very broad wing which is about 50% broader than the central disk.

(17) The apex of the wing is rather flat, with a notch between the lateral halves.

(18) The wing is attached at about the middle of the prophyll.

(19) Blades of the leaves are spreading in habit.

(20) Group 52 hairs cover most of the inner surface of the dewlap and sometimes extend across the midrib.

(21) The outer auricle is usually short deltoid in shape, the inner auricle is long lanceolate.

(22) The ligule is broadly crescent-shaped with broad lozenge.

(23) Both the upper and lower margins of the ligule are irregularly toothed.

(24) Marginal cilia of the ligule are ¼ to ⅓ millimeter tall and occur mostly on the teeth thus accentuating the toothed appearance.

(25) This new variety blooms abundantly at Clewiston, Fla., and is male sterile at this location.

What is claimed is:

1. The new and distinct variety of sugarcane herein shown and described, identified by the combination of the characteristics enumerated above.

No references cited.

ROBERT E. BAGWILL, *Primary Examiner.*